US008040248B2

United States Patent
Fridthjof (10) Patent No.: US 8,040,248 B2
(45) Date of Patent: *Oct. 18, 2011

(54) DEVICE FOR DETECTION OF SURFACE CONDITION DATA

(75) Inventor: Jack Fridthjof, Viby J (DK)

(73) Assignee: LIWAS APS (DK)

( * ) Notice: Subject to any disclaimer, the term of this patent is extended or adjusted under 35 U.S.C. 154(b) by 0 days.

This patent is subject to a terminal disclaimer.

(21) Appl. No.: 12/634,386

(22) Filed: Dec. 9, 2009

(65) Prior Publication Data

US 2010/0085175 A1    Apr. 8, 2010

Related U.S. Application Data (63) Continuation of application No. 10/549,354, filed as application No. PCT/DK2004/000168 on Mar. 15, 2004, now Pat. No. 7,652,584.

(30) Foreign Application Priority Data

Mar. 14, 2003    (DK) .......................... PA 2003 00386

(51) Int. Cl.
*G08B 19/02*    (2006.01)
(52) U.S. Cl. ................... 340/580; 340/905; 250/339.11; 73/649
(58) Field of Classification Search ................ 340/905, 340/901, 580, 581; 250/339.11, 341.8, 559.09; 356/369, 364; 73/649, 73, 170.21

See application file for complete search history.

(56) References Cited

U.S. PATENT DOCUMENTS 3,836,846 A    9/1974    Overall et al.
4,274,091 A *    6/1981    Decker .......................... 340/583

(Continued)

FOREIGN PATENT DOCUMENTS

DE    27 12 199    9/1978

(Continued)

OTHER PUBLICATIONS

English Abstract of patent EP 0558927—Sep. 8, 1993.

(Continued)

*Primary Examiner* — Eric M Blount
(74) *Attorney, Agent, or Firm* — Cantor Colburn LLP (57) ABSTRACT

A device is disclosed for detection of surface properties or conditions, in particular detection of water, snow and ice and in particular to road surfaces by means of detector means mounted on individual vehicles, and transmitting the data from the vehicle, preferably together with position data of the vehicle, to be used by drivers of other vehicles for warning of slippery road conditions ahead of the vehicle. According to a particular aspect, it has been realised that the fact that polarized light which is mirror reflected by e.g. ice or water on a surface, preserves its polarization, whereas polarized light which is diffuse reflected largely becomes depolarized, may be utilised to separate the two types of reflection and thus provide a much more compact sensor device for surface properties, in which the light may be emitted close to or parallel to the road surface normal.

21 Claims, 5 Drawing Sheets

U.S. PATENT DOCUMENTS

| | | | |
|---|---|---|---|
| 4,690,553 A | 9/1987 | Fukamizu et al. | |
| 4,786,815 A | 11/1988 | Walker et al. | |
| 4,844,584 A | 7/1989 | Miyagawa | |
| 5,198,875 A | 3/1993 | Bazin et al. | |
| 5,218,206 A * | 6/1993 | Schmitt et al. | 340/583 |
| 5,243,185 A * | 9/1993 | Blackwood | 340/583 |
| 5,428,544 A | 6/1995 | Shyu | |
| 5,475,370 A * | 12/1995 | Stern | 340/583 |
| 5,541,413 A * | 7/1996 | Pearson et al. | 250/301 |
| 5,557,040 A | 9/1996 | Inenaga et al. | |
| 5,617,076 A * | 4/1997 | Stern | 340/583 |
| 5,650,610 A * | 7/1997 | Gagnon | 340/583 |
| 5,652,522 A | 7/1997 | Kates et al. | |
| 5,652,655 A * | 7/1997 | Uno et al. | 356/600 |
| 5,699,056 A | 12/1997 | Yoshida | |
| 5,710,554 A | 1/1998 | Pettler et al. | |
| 5,844,682 A | 12/1998 | Kiyomoto et al. | |
| 5,852,243 A | 12/1998 | Chang et al. | |
| 5,962,853 A | 10/1999 | Huth-Fehre et al. | |
| 5,963,148 A | 10/1999 | Sekine et al. | |
| 6,166,645 A * | 12/2000 | Blaney | 340/583 |
| 6,173,231 B1 | 1/2001 | Chojnacki | |
| 6,178,374 B1 | 1/2001 | Mohlenkamp et al. | |
| 6,370,475 B1 | 4/2002 | Breed et al. | |
| 6,538,578 B1 | 3/2003 | Doherty | |
| 6,680,479 B1 * | 1/2004 | Murray | 250/339.1 |
| 6,720,920 B2 | 4/2004 | Breed et al. | |
| 7,119,336 B2 * | 10/2006 | Allen et al. | 250/341.8 |
| 7,271,737 B1 | 9/2007 | Hoffberg | |
| 7,652,584 B2 * | 1/2010 | Fridthjof | 340/580 |

FOREIGN PATENT DOCUMENTS

| | | |
|---|---|---|
| DE | 30 23 444 | 1/1981 |
| DE | 32 05 129 A1 | 9/1983 |
| DE | 43 00 896 | 4/1994 |
| EP | 0 005 696 | 12/1979 |
| EP | 0 558 927 | 9/1993 |
| EP | 0 720 137 | 7/1996 |
| JP | 03 110408 | 10/1991 |
| JP | 06 307838 | 11/1994 |
| JP | 2002008198 | 1/2002 |

OTHER PUBLICATIONS

English Abstract of patent DE 4300896—Apr. 21, 1994.
English Abstract of patents EP 0005696 and DE 2712199—Dec. 12, 1979.
English Abstract Not Available for DE 3023444, however, this patent is related to US 4690553.
English Abstract of patent JP 06307838—Apr. 11, 1994.
English Abstract of patent JP 03110408—Oct. 5, 1991.

* cited by examiner

DEVICE FOR DETECTION OF SURFACE CONDITION DATA

CROSS REFERENCE TO RELATED APPLICATIONS

This application is a Continuation of U.S. application Ser. No. 10/549,354, filed May 8, 2006, which is a National Stage Application of PCT/DK04/00168 filed on Mar. 15, 2004, and claims benefit of the priority filing date of Mar. 14, 2003 of Danish Patent Application No. PA 2003 00386 under the provisions of 35 U.S.C. 119. The contents of U.S. application Ser. No. 10/549,354, PCT/DK04/00168, and PA 2003 00386 are incorporated by reference herein in their entirety.

TECHNICAL FIELD OF THE INVENTION

The present invention relates to detection of surface properties or conditions, in particular detection of water, snow and ice and in particular to road surfaces by means of detector means mounted on individual vehicles. The detected properties are according to one aspect of the invention transmitted from the vehicle, preferably together with position data of the vehicle, to be used by drivers of other vehicles for warning of slippery road conditions ahead of the vehicle.

BACKGROUND

Detectors for determining the properties of a road surface are well known in the art, including stationary detectors arranged along the roadside and above the surface, detectors arranged beneath the road surface as well as detectors arranged on the vehicles.

A simple principle for contact-less measurement is disclosed in U.S. Pat. No. 4,274,091 by Decker, in which a series of light pulses is directed towards the road surface by a light emitter with a chopper wheel, and the intensity of the reflected light is measured with one receiver. The amplitude of the signal measured by the receiver indicates the presence or absence of ice on the road surface.

Another principle is disclosed in U.S. Pat. No. 4,690,553 by Fukamizu et al., in which an infrared light emitter directs a ray towards the road surface, and two receivers are arranged to measure the mirror reflected light and the scattered or diffuse reflected light, respectively. The ratio of the output from the two receivers provides information of the road surface properties. Utilisation of the reflection of infrared light to measure the road surface properties is also known from e.g. DE 2,712,199, EP 0,005,696 and DE 3,023,444.

Other principles involves the use of acoustic waves as disclosed in Japanese patent application JP 03-110408 by Hiroshi and Masami, The use of microwaves is disclosed e.g. in U.S. Pat. No. 5,652,522 by Kates and Butler and in U.S. Pat. No. 3,836,846 by Overall and deKoning, the use of microwaves in combination with a laser light beam as disclosed in Japanese patent application JP 06-307838 by Takaharu, the use of multiple wavelength regions of infrared light is disclosed in U.S. Pat. No. 5,218,206 and in U.S. Pat. No. 5,962,853.

All the disclosed measurement principles and other similar principles may be utilised for the device and the system of the present invention. The different arrangements of the sensors have each their drawback. Sensors arranged along the roadside and above the road surface have to be about 4.5 meters above to road surface to allow all types of vehicles to pass, and the air between the sensor and the road surface will be contaminated with particles raised from the road surface by the passing vehicles, in particular when the road surface is wet or covered with sled or snow, and the reliability of the sensor is therefore low under the weather conditions at which the warnings of slippery surface conditions are of importance. Sensors embedded in the road surface and measuring the properties thereof from below through a transparent lid, suffer from contamination of the upper surface of the lid and development of scratches, which ruin the operation of the sensor. Sensors mounted on the vehicle measure from above close to the road surface, but provide only information about the road surface properties at the position of the vehicle, which often is too late for the driver of the vehicle to take measures, in particular under changing properties of the road surfaces and during weather conditions where only local areas of the road surfaces have slippery conditions.

BRIEF SUMMARY OF THE INVENTION

Thus, it is an object of the present invention to provide a devise for determining the properties of the road surface with high reliability under the relevant weather conditions and providing the relevant data to the drivers of the vehicles before they enter the area where the properties are determined.

This object is achieved by the present invention by equipping vehicles with road surface sensor device for mounting in a vehicle, comprising detector means for contact-less detection of the surface properties of the road surface and providing an output accordingly as discussed above, where the device further comprises transmission means for receiving said output from the detector means and performing a wireless transmission of road surface property data based thereon to a receiver exterior to the vehicle, wireless receiver means adapted to receive radio transmissions of data from transmission means of devices similar to the device itself, i.e. stationary or arranged on other vehicles and data output means for receiving an input from the receiver means and presenting an output perceivable by the driver of the vehicle based thereon.

With this solution, a system of a plurality of mobile sensors may be provided which are arranged very close to the part of the road surface on which the vehicles drive, and they may therefore determine the relevant properties of the road surface from the most advantageous position. These very reliable data are transmitted and received, so that the system as a whole holds reliable data for at least a part of the road surfaces of an area and may distribute these data to the drivers of the vehicles before they enter the area where the data were determined without the requirement for a central stationary unit as disclosed in EP 0 720 137 to process the transmitted data and transmit the results to the individual units in the vehicles.

Another problem of the known surface conditions sensors for mounting e.g. on a vehicle is that they are very sensitive to the distance between the sensor and the surface because the light emitted towards the surface has an angle to the surface normal. Also, in the case of sensors detecting the mirror reflected light and the scattered or diffuse reflected light a vertical distance between the detectors for the two types of reflection is necessary to obtain the spatial separation between the two and a compact sensor device cannot be obtained.

Thus, it is an object of the present invention to provide a sensor device, which overcomes these known problems and drawbacks.

This is obtained with the sensor device according an aspect of the present invention, in which it has been realised that the fact that polarized light which is mirror reflected preserves its polarization, whereas polarized light which is diffuse reflected largely becomes depolarized, may be utilised to separate the two types of reflection and thus provide a much more compact sensor device, in which the light may be emitted close to or parallel to the road surface normal.

Also, sensor devices based on detection of mirror reflected light as well as diffuse reflected light suffer from the drawback that water as well as ice enhances mirror reflection, and the distinguishing between the two is rather uncertain, and it is therefore an object of the present invention to provide a sensor device, where this uncertainty is reduced. This is provided by an aspect of the present invention, wherein such device is combined with one or more other measurement devices which by themselves are simple and insufficient to provide reliable data for the surface properties, but which in combination with a device detecting the mirror and diffuse reflected light can produce data of the surface properties of a high certainty.

Other advantages of the present invention, preferred embodiments and refinements thereof and the associated advantages are disclosed below.

Thus, the present invention relates in a first aspect to a road surface property device for mounting in a vehicle, comprising
a sensor device having a radiation emitter directed towards the road surface and at least one detector for detecting the radiation reflected from the road surface and providing an output accordingly, and data processing means for processing the output from the at least one detector to determine surface properties of the road and providing an output accordingly,
transmission means for receiving said output from the sensor device and conducting a wireless transmission of road surface property data based thereon to a receiver exterior to the vehicle, wherein the device further comprises wireless receiver means adapted to receive radio transmissions of data from transmission means of devices similar to the device itself, and
data output means for receiving an input from the receiver means and presenting an output perceivable by the driver of the vehicle based thereon.

The radiation may, as discussed previously, be sonic or electromagnetic or a combination thereof, and it is preferred that radiation in the infrared range is used, as the reflection and scattering of infrared light is particularly sensitive to the occurrence of ice particles. Another preferred embodiment includes a plurality of receivers, such as a linear or two-dimensional CCD (Charge-Coupled Device) camera or other camera device, where the pattern of the output from the receivers is analysed.

The transmitter may be any type of radio based transmitter, but it is preferred to use a public wireless data communication network as the ones used for cellular telephones and data transmission, such as the GSM (Global System for Mobile Communications) or GPRS (General Packet Radio Service).

The device will, together with devices in one or more vehicles on the same road or in the same area or optionally also stationary device constitute a network for collection and distribution of road surface property data, and the quality of the output from the network will be improved for each extra participant. It is also important to notice that the collection of data is continuous and that useful data are collected from devices in vehicles that are moving slowly or are at a stand still, which is often the situation when the roads are slippery.

It is preferred that the device comprises position means for generating position data for estimation of the current position of the device, and that the transmission means is arranged to transmit said position data. Thereby, the coupling of the road surface property data and the position data may be made immediately. Another use of the position data is to filter data from other devices of the system to obtain data relevant to receive and display for the individual device. This filtering may take place locally in the device itself, which e.g. receives data from all similar devices, or the filtering may be performed centrally based on position data received from the devices. Furthermore, it is also preferred that the time of determining the road surface property data are generated and associated with said data.

The position means may be one of a number of different known position determining means, such as means for generating said position data from communication with a wireless data communication network constituted by a plurality of stationary transceiver stations. Another known position determining means comprises means for satellite based position estimation such as the GPS (Global Positioning System). Alternatively, the position may be determined by a system exterior to the device, e.g. based on triangulation from a number of transceiver stations of a wireless data transmission network.

The transmitted data from the device may be received and used in various different ways as discussed previously. However, it is preferred that the device comprises wireless receiver means and data output means for receiving an input from said receiver means and presenting an output perceivable by the driver of the vehicle based thereon. The receiver means may receive data from other, similar devices or from a central, stationary transmitter that receives and transmits data from a plurality of such devices. Another advantage of including a wireless receiver means is that the device and the system may be employed to transmit information from e.g. the police authorities or the road authorities to the drivers of the vehicles, preferably in a particular area or driving towards a particular road section. The driver will also receive the relevant information from the network even if the device of the vehicle is out of order or too clogged with dirt to function correctly.

The data output means may further be arranged for receiving an input from the detector means and presenting an output perceivable by the driver of the vehicle based thereon.

A further feature of the device is preferably that the transmission means of the device are adapted to transmit operational data of the vehicle, such as indication of an emergency breaking, output from an antilock braking system (ABS) of the vehicle and/or the output from an accelerometer of the vehicle. The purpose is to provide warnings to other drivers of operational conditions that indicate slippery conditions or emergency situations. A system for distributing data from the ABS or similar systems of the vehicles to other vehicles is disclosed in Japanese patent application JP 2001-107041 by Yukio and Hiroshi, and the disclosed system and many of the details thereof may be used as a supplement to the system of the present invention. However, as the system of JP 2001-107041 only provides signals when a wheel of a vehicle actually slips relatively to the road surface, it cannot replace the system of the present invention, which provides data of the actual condition of the road surface, regardless of whether the wheels of a vehicle have slipped on the surface or not and also from vehicle moving slowly or are stopped, as often occurs during periods with slippery road conditions.

The present invention relates furthermore to the system comprising a plurality of devices as disclosed above, each mounted in a separate vehicle.

It is preferred that system comprises position determination means for determining the position of each of said devices. The position data may be obtained from the individual devices or may be obtained from a central system, e.g.

from triangulation based on a number of transceiver stations of a wireless data transmission network. The triangulation may be performed from the devices in the vehicles or from the stationary system.

The means for distributing the received data may preferably comprise wireless data transmission means for transmitting the data to e.g. receivers in vehicles and/or to receivers in stationary signs arranged along the roads.

The means for distributing the received data may in one embodiment be adapted to distribute the associated position data together with the road surface property data associated thereto, so that the filtering of the distributed data is performed at the receiving parts. The means for distributing the received data may additionally or alternatively be adapted to distribute data dedicated to receiver means of individual ones of said devices in accordance with position data of said individual devices.

The system may further comprise stationary detector means arranged along the roads for contact-less detection of the surface properties of the road surface and providing an output accordingly, the output being distributed by the distribution means similarly to the received data.

The means for distributing the received data comprises a plurality of visual communication devices, i.e. signs with display means, arranged along roads for distributing information to the drives of vehicles on said roads based on the received road surface property data.

According to a second aspect, the present invention relates to a sensor device for non-contact detection of conditions of a surface, such as a road surface, the system comprising a light source for emitting light towards the surface,
a first detector arranged for receiving a portion of said emitted when reflected from said surface and producing a first output according to the intensity thereof,
a second detector arranged for receiving a portion of said emitted when reflected from said surface and producing a second output according to the intensity thereof, and
control means for receiving and evaluating the received output from the detectors based on the amount of diffuse reflected and mirror reflected light, wherein the sensor device further comprises
a first linear polarization filter arranged in the path of the light from the light source and to the surface for the polarization of the emitted light, and
a second linear polarization filter arranged in the path of the light between said surface and one of the first detector and the second detector.

Thus, by means of utilising the fact that that polarized light which is mirror reflected preserves its polarization, whereas polarized light which is diffuse reflected largely becomes depolarized, to separate the two types of reflection and thus provide a much more compact sensor device, in which the light may be emitted close to or parallel to the road surface normal. The light may be emitted in a direction substantially perpendicularly, i.e. within 15-20° from the surface normal, preferably within 10° from the surface normal, such as within 6°, and the paths of the reflected light to the detectors may be as close as a suitable arrangement requires and even coincident with each other as well as with the path of the emitted light. The sensor device may therefore be very compact, which allows for an easy installation, adjustment and maintenance of the device on a vehicle. Also, the sensitivity of the sensor device towards variations in the distance from the device to the road surface may be reduced.

In one embodiment, the direction of polarization of the second filter is parallel to the direction of polarization of the first filter. In particular, the first and the second filter may in one embodiment be the same filter as demonstrated below with reference to the figures. In this embodiment, a beam splitter is arranged between the first polarization filter and the light source for the diversion of a portion of the light reflected from the surface into said detector. However, the second filter may be perpendicular to the direction of polarization of the first filter so that the detector receives the mirror reflection plus about half of the diffuse reflection.

Furthermore, the sensor device may comprise a third polarization filter arranged in the path of the light between said surface and the other one of the first detector and the second detector, wherein the direction of polarization of the third filter is perpendicular to the direction of polarization of the first and the second filter. In this preferred situation, one detector receives the mirror reflection plus about half of the diffuse reflection, whereas the other detector received the diffuse reflection only.

In a particular embodiment, the paths of emitted and reflected light are coincident and the sensor device comprises a first beam splitter arranged in the path of the light from the first linear polarization filter and to the surface for the diversion of a portion of the light reflected from the surface, including mirror reflected light as well as diffuse reflected light, into a second path, and a second beam splitter arranged in the second path for the diversion of a portion of the light in the second path into the first detector and the transmission of a portion of the light in the second path into the second detector. The first and the second beam splitters should be substantially insensitive to polarization of the light.

A reference light source may advantageously be included, which is arranged to emit light substantially in the direction and path of the first light source, wherein the reference light source emits light of a wavelength, such as infrared light, on which said polarization filters of the device have substantially no effect, so that the detection of the light from the reference light source by the first and second detector may be used for verification of the function of the system.

In order to enhance the discrimination between the mirror reflection from water and ice, the sensor device may further comprise a light source for emitting light within the wavelength range of 930 nm to 970 nm towards the surface and an absorption detector for receiving the reflection of said emitted light and producing an output to the control means accordingly. The absorption of infrared light in this wavelength range by water is high, in particularly about 950 nm, but not as significantly high as about 1450 nm. However, equipment for measuring the absorption about 950 nm only costs a fraction of the equipment for measuring the absorption about 1450 nm, and when used in combination with the disclosed sensor device, the reliability of the measurements of absorption about 950 nm is sufficient to obtain a reliable result for the surface properties.

The sensor device may furthermore be combined with a retro-reflection device comprising a light source for emitting light towards the surface, the path of the light having an angle in the range of 15° to 70°, preferably in the range of 25° to 60° to the surface normal and a retro-reflection detector arranged for receiving the retro-reflection of said emitted light in said path and producing an output to the control means accordingly. The retro-reflection sensor is used for the detection of ice crystals on the surface, i.e. mainly the presence of snow or rime.

The sensor device may in yet another embodiment be combined with a sensor device for colour separation of reflected polychromatic light, comprising a source of polychromatic visible light, such as white light, and two or preferably three detectors for detection of the amount of light in various wavelength range, preferably within the red, green and blue range, respectively, of the reflected light and providing outputs to the control means. The results may be used to verify the measurements of the mirror and diffuse reflected light and may also be used to correct these measurements due to the features of the surface that are detected by the colour separation, e.g. whether the surface is made from concrete or asphalt, is painted etc. It is preferred that the wavelength ranges each comprises a range within the visible wavelength range.

The sensor device may in yet another embodiment be combined with a noise sensor for receiving the noise from the vehicle travelling along a road and producing an output to the control means accordingly. The analysis of the noise collected by e.g. a microphone is performed by the control means and an example of how this analysis may be conducted is disclosed in U.S. Pat. No. 5,852,243 by Chang et al.

The road surface sensor device according to the first aspect of the present invention may have a sensor device according to the second aspect of the invention.

The present invention further relates to a road surface detector means to be mounted on a vehicle for contact-less detection of the surface properties of the road surface and providing an output accordingly, comprising a radiation transmitter directed to the road surface and at least one receiver for receiving the radiation returned from the road surface and providing an output accordingly, wherein the detector means comprises washing means for the transmitter and the at least one receiver for recurrently flushing thereof. This detector means may be used with the device and the system disclosed previously. The purpose of the washing means is to improve the reliability of the detector by removing dirt that prevents the transmitter and the receiver from operating at optimal visual contact with the road surface. The washing means may be actuated by a surveillance device that supervises the operation of the detector means. It is particularly preferred that said washing means is connected to and operates concurrently with a windshield washer system of the vehicle. Thereby, the driver of the vehicle functions as the surveillance device, as the windshield will be unclear to an extent and at a rate that is parallel to the same conditions for the detector means.

It is of importance to the credibility and reliability of the device that the output is provided substantially constantly, and it is preferred that the device comprises a self-check circuit that provides an "Out-of-order" output if the device is not operating properly. The output may be used to control the operation of separate washing means for flushing the transmitter and the at least one receiver recurrently.

Furthermore, the present invention relates to a road surface detector means to be mounted on a vehicle for contact-less detection of the surface properties of the road surface and providing an output accordingly, comprising a radiation transmitter directed to the road surface and at least one receiver for receiving the radiation returned from the road surface and providing an output accordingly, where at least one receiver of the detector means comprises a shutter device for allowing a temporal access of radiation to the receiver for a period of 1/10 to 1/50,000 seconds, preferably of 1/50 to 1/10,000 seconds. This detector means may be used with the device, the system and the detector means disclosed previously. The purpose of providing the receiver with a shutter device is to enhance the sharpness of the reflection and/or the scattering received from the road when the vehicle moves at high velocity. A similar enhancement of the sharpness is not achieved by pulsing the radiation transmitter as known in the art.

According to another aspect of the present invention, a sensor device is provided, such as the one of the present invention as disclosed previously, for non-contact detection of conditions of a surface, such as a road surface, the system comprising a light source for emitting light towards the surface, a first detector arranged for receiving a portion of said emitted when reflected from said surface and producing a first output according to the intensity thereof, a second detector arranged for receiving a portion of said emitted when reflected from said surface and producing a second output according to the intensity thereof, and control means for receiving and evaluating the received output from the detectors based on the amount of diffuse reflected and mirror reflected light, wherein the device further comprises one or more arrangements for detecting conditions of the surface selected from a group comprising:

an infrared light source for emitting light within the wavelength range of 930 nm to 970 nm towards the surface and an absorption detector for receiving the reflection of said emitted infrared light and producing an output to the control means accordingly, a light source for emitting light towards the surface, the path of the light having an angle in the range of 15° to 70°, preferably in the range of 25° to 60° to the surface normal and a retro-reflection detector arranged for receiving the retro-reflection of said emitted light in said path and producing an output to the control means accordingly, a light source for emitting polychromatic light towards the surface and at least two range detectors, preferably at least three range detectors, arranged to detect each a wavelength range of the reflection of said emitted light and producing an output to the control means accordingly, and a noise sensor for receiving the noise from a vehicle travelling along a road and producing an output to the control means accordingly, on which vehicle the device is arranged.

BRIEF DESCRIPTION OF THE DRAWING

Embodiments of the present invention are disclosed in the accompanying drawing for the purpose of exemplifying the present invention without thereby limiting the scope of the invention and the protection conferred.

DETAILED DESCRIPTION OF AN EMBODIMENT

Figure 1:
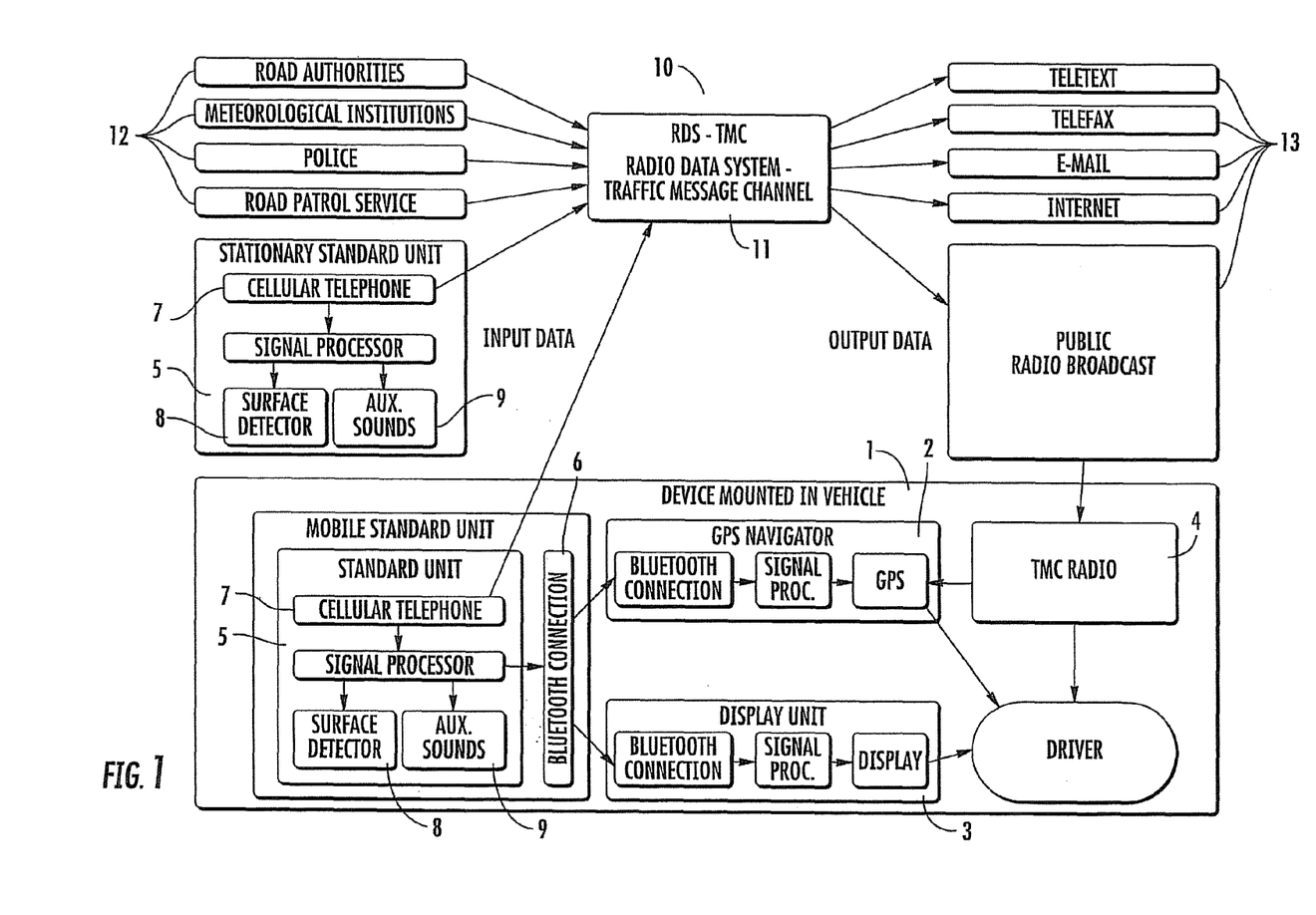
FIG. 1 is a diagram of the system with a device in a vehicle and a central, stationary part.

The system shown in FIG. 1 comprises a device 1 for mounting in a vehicle, comprising a standard GPS device 2 used e.g. for a navigation system, a display unit 3, which also may be used for other purposes, e.g. for the navigation system, a radio 4 for receiving TMC, and a standard sensor device 5, communicating with the GPS device 2 and the display unit 3 via a wireless Bluetooth data connection 6. The standard sensor device 5 may also be used at stationary roadside measurement stations 5'. A radio transmitter 7 of the standard sensor device 5 communicates road surface property data achieved from the road surface detector means 8, from the GPS device 2 and other possible sources 9, such as the ABS, to the stationary part 10 of the system as well as to similar devices 1 mounted in other vehicles by means of transmitting the data as data packages on a common communication channel. The mutual direct exchange of data between similar devices 1 will normally be limited in distance, but the data being most interesting for the driver of a given vehicle are normally data obtained by nearby vehicles, and in one, simple embodiment of the system, the stationary part 10 is not established and the mutual exchange of data between devices 1 takes place only by means of direct exchange of data and not via the stationary part 10.

The stationary part 10 includes a central unit 11 that receives data from the devices 1 in vehicles, from stationary devices 5' and from various sources, 12, such as the police department and the meteorological institution providing whether forecasts. The data are distributed to a plurality of users 13, such as roadside signs, radio receivers 4 in vehicles, an Internet home page, etc.

Alternatives may be used for the different parts of the system as described previously. The GPS device 2 may be replaced by a position estimation system based on the radio transmitter 7 and triangulation from a plurality of transceiver stations constituting a data communication system with which the radio transmitter 7 communicates. The triangulation may be performed from the device 1 or from the stationary part 10 of the system. Another alternative for estimating the position is to perform a short-range radio communication between the device 1 and a plurality of stationary stations arranged along the roadside, e.g. equipped with signs for providing alerts to the drives of the passing vehicles of ice on the road surface ahead. This short-range communication may be used to communicate road surface property data to the stationary system and simultaneous provide information about the position of the vehicle when the data were obtained.

The radio 4 which is used to receive road surface property data from the stationary part 10 of the system may be replaced by a radio receiver, e.g. a mobile phone device, which constantly receives road property data transmitted either from other devices of other vehicles or from a stationary system, and filter the data based on the position data included in the received data and vehicle position data received from the position estimation system of the device. Alternatively, the road surface property data may be filtered at the stationary part 10 of the system based on vehicle position data received from the device 1 and only the relevant road surface property data are transmitted with a unique user identification to the device 1, where a receiver filter the received data based on the user identification included in the received data. The received, relevant data is then presented to the driver, preferably by means of the display unit 3 and/or an audio signal in case the road condition requires a warning to the driver.

Figure 2:
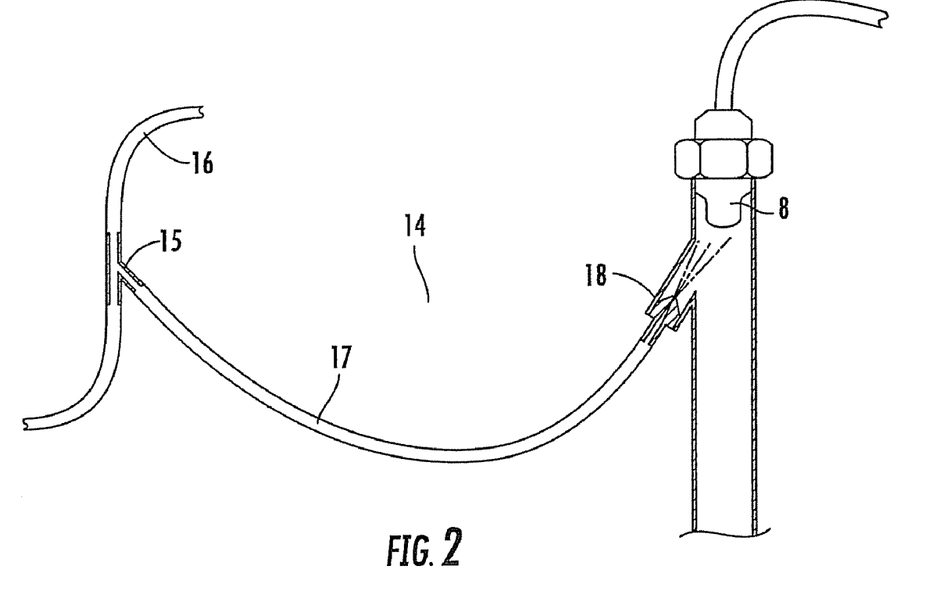
FIG. 2 shows a washing device.

A road surface detector means 8 mounted on a vehicle for contact-less detection of the surface properties of the road surface and providing an output accordingly is shown in FIG. 2. The detector means 8 comprises a radiation transmitter directed to the road surface and at least one receiver for receiving the radiation returned from the road surface and providing an output accordingly. The detector means 8 comprises washing means 14 for the transmitter and the at least one receiver for recurrently flushing thereof, comprising a Y-branch 15 in the tube 16 connecting the pump of the windshield washer system of the vehicle and the nozzles for distributing the cleaning liquid onto the windshield. A second tube 17 directs a part of this liquid to a nozzle 18 that flushes the detector means 8 every time the driver of the vehicle actuates the windshield washer system.

Various embodiments of sensor devices according to the present invention are shown in FIGS. 3-6. They all comprises a light source 19 that emits light in the visible range towards a surface 20, in particularly the surface of a road, and two detectors 21, 22 for detecting the reflection of the emitted light from the surface 20 and providing an output accordingly to a control unit 23, a linear polarization filter 24 between the light source 19 and the surface 20, so that the light that meets the surface 20 is polarized, and a linear polarization filter 25 in front of one of the detectors 21, 22, so that the variation in the output from the two detectors 21, 22 will be representative for the variation in mirror reflected light and diffuse reflected light from the surface 20, as the mirror reflected light will preserve its original polarization whereas the diffuse reflected light substantially will become depolarized. Thus, the light source 19 and the detectors 21, 22 may be situated very closely together and the angle between the incoming and reflected light is normally within the range of 0° to 15°, and the angle between the incoming light and the surface normal will normally be within the range of 0° to 6°. The angles on the figures are exaggerated in order to illustrate the principles more clearly. Thereby, the sensor is quite insensitive to the actual vertical distance between the sensor and the road surface 20 so that the same sensor may be installed in different types of vehicles and the quality of the output will not be deteriorated by the variations in the vertical distance during operation of the vehicle.

Figure 3:
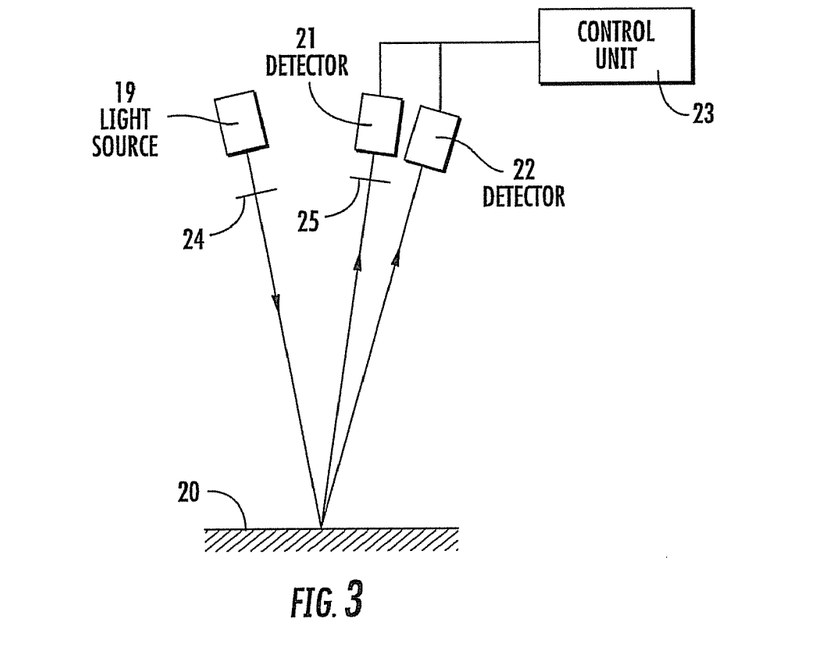
FIG. 3 shows a first configuration of a sensor device according to the present invention.
Figure 4:
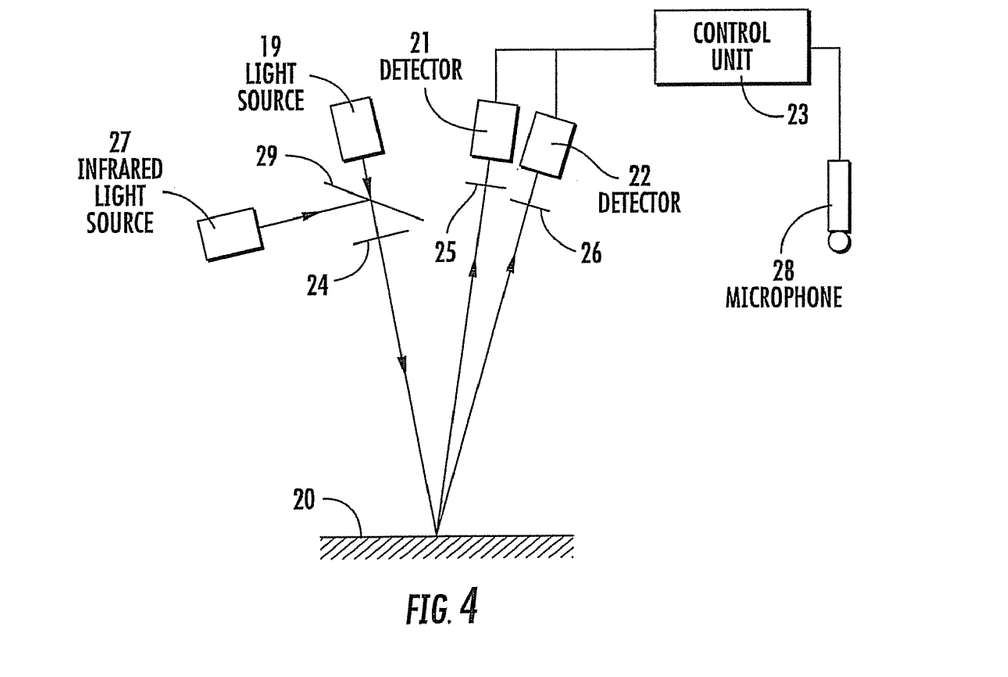
FIG. 4 shows a second configuration of a sensor device according to the present invention.

The sensor device shown in FIG. 3 has a very simple configuration, in that the light source 19 and the two detectors 21, 22 are arranged side by side so that the light follows a separate path for each of the three. However, due to the small angles between the paths, the two detectors 21, 22 will be subjected to substantially the same intensity of mirror reflected light and diffuse reflected light. A linear polarization filter 25 is arranged in the path of the reflected light to one of the detectors 21 and the filter 25 has a direction of polarization perpendicular to the polarization direction of the filter 24 in front of the light source 19, so that the detector 21 will receive the diffuse reflected light and produce an output to the control means 23 accordingly, whereas the other detector 22 will receive the mirror reflected light as well as the diffuse reflected light and produce an output to the control means 23 accordingly. The difference between the two outputs will be a measure of the intensity of the mirror reflected light. The configuration may be improved with another linear polarization filter 26 arranged in front of the other detector 22 and with a polarization direction parallel to the one of the filter 24 in front of the light source 19 as shown in FIG. 4. Thereby, the other detector 22 will receive the mirror reflected light plus only about half of the diffuse reflected light and produce an output to the control means 23 accordingly. Thus, the amplitude variation of the output from the other detector 22 due to the presence of mirror reflection will be enhanced which improves the signal-to-noise ratio of the device.

In the embodiment of the sensor device shown in FIG. 4, the configuration has been improved with the presence of two extra features, an infrared light source 27 used as a reference light for verification of the function of the system, and a microphone 28 for receiving the noise form the vehicle travelling along a road and producing an output to the control means accordingly. Both features may be implemented either alone or in combination, into each of the shown embodiments of the invention as well as other embodiments thereof. The infrared reference light source 27 is arranged to emit light substantially in the direction and path of the first light source 19 by means of a beam splitter 29 arranged in that path. The polarization filters 24, 25, 26 have substantially no effect on the infrared light, so that the detection of the light from the reference light source by the first and second detector may be used for verification of the function of the system, correction for temporarily reduced transmittance of the light e.g. due to soiling of lenses or transparent covers, etc. In a preferred embodiment, the infrared reference light source 27 emits light within the wavelength range of 930 nm to 970 nm, which is one of the wavelength areas where water in particular absorbs radiation, and the light source 27 may be used for spectroscopic measurement of whether liquid water is present on the surface, which in combination with the measurements of diffuse and mirror reflected light may give a precise indication of the surface conditions of the road. By measuring the variations in intensity of this reference light by means of the detectors 21, 22 while the first light source 19 is turned off, the presence of water on the road surface may be detected, and the control means 23 may thereby distinguish between mirror reflection from water and from ice, which does not absorb infrared light to the same degree.

The analysis of the noise collected by the microphone 28 is performed by the control means 23 and an example of how this analysis may be conducted is disclosed in U.S. Pat. No. 5,852,243 by Chang et al. This analysis is likewise used as a supplement to the measurement of the diffuse and mirror reflected light to distinguish between the presence of ice or water on the road surface.

Figure 5:
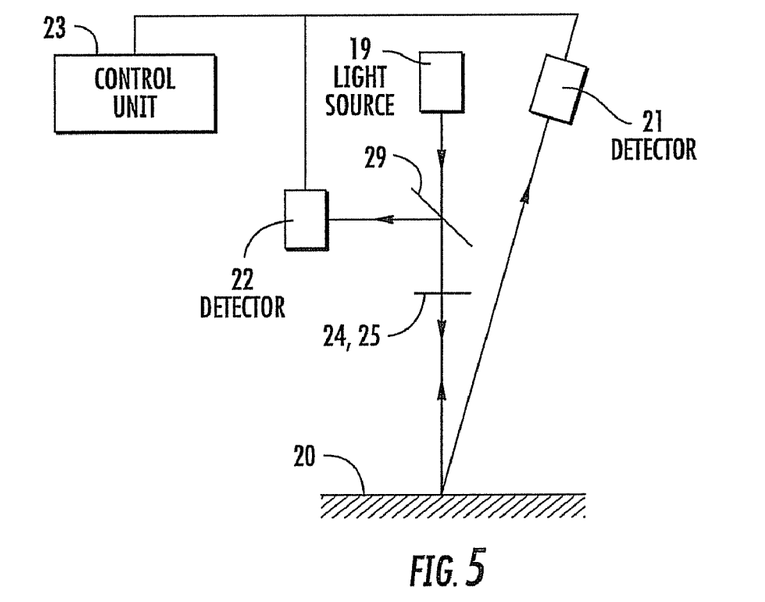
FIG. 5 shows a third configuration of a sensor device according to the present invention.
Figure 6:
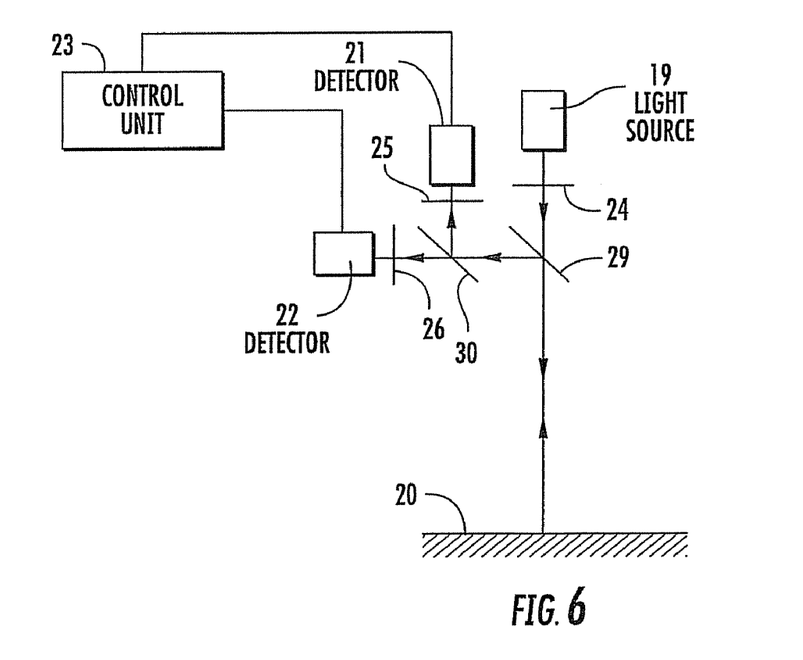
FIG. 6 shows a fourth configuration of a sensor device according to the present invention.

In FIG. 5, yet another configuration of the sensor device is shown, in which only one and the same linear polarization filter 24, 25 is used for the light emitted from the light source 19 towards the surface 20 and the light reflected from the surface towards one of the detectors 22. The light source 19 is directed perpendicularly towards the surface 20 and a beam splitter 29 is arranged in the path of the reflected light towards the detector 22, which in this configuration is identical to the path of the light from the light source 19 towards the surface 20. In FIG. 6, another beam splitter 30 is added for dividing the light from the first beam splitter 29 for both detectors 21, 22 so that all light to and from the sensor device may be passed through a small opening or thin tube, which is easy to maintain clean, and the sensitivity to the distance between the sensor device and the surface 20 may be substantially completely eliminated.

Figure 7:
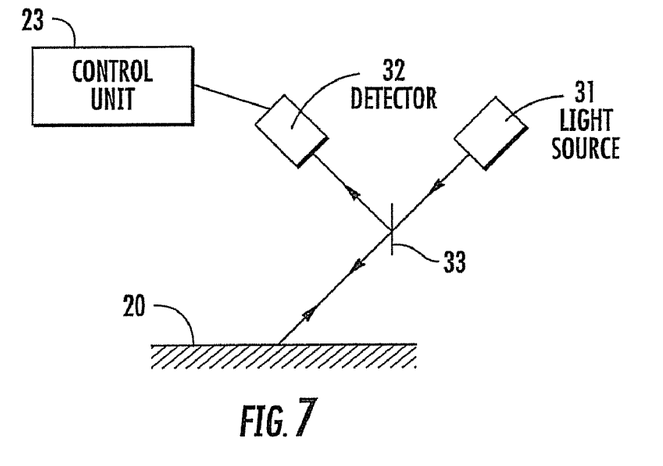
FIG. 7 shows a retro-reflection sensor according to an aspect of the present invention.
Figure 8:
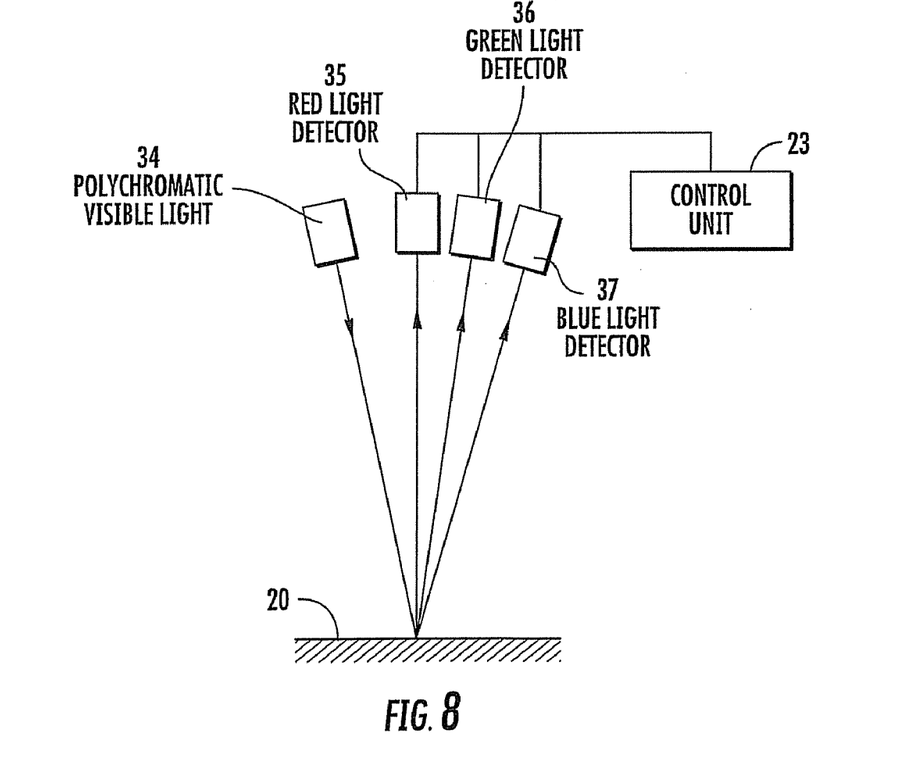
FIG. 8 shows a sensor device with colour separation according to the present invention.

Two other devices that may be used a supplement to the measurement of the diffuse and mirror reflected light to distinguish between the presence of ice or water on the road surface are shown in FIGS. 7 and 8.

A retro-reflection sensor is shown in FIG. 7, comprising a light source 31, which emits light at an angle of 45° towards the surface and a detector 32 arranged to receive the retro-reflected light by means of a beam splitter 33 and producing an output accordingly to the control means 23. The retro-reflection sensor is used for the detection of ice crystals on the surface, i.e. mainly the presence of snow or rime.

A sensor device for colour separation of reflected polychromatic light is shown in FIG. 8, comprising a source 34 of polychromatic visible light, such as white light, and three detectors 35, 36, 37 for detection of the amount of light within the red, green and blue range, respectively, of the reflected light and providing outputs to the control means 23. The results may be used to verify the measurements of the mirror and diffuse reflected light and may also be used to correct these measurements due to the features of the surface that are detected by the colour separation, e.g. whether the surface is made from concrete or asphalt, is painted etc.

All the embodiments are shown in principle drawings, and it will be straightforward for the skilled person to add necessary constructive details, transparent covers optics etc.

The invention claimed is:

1. A road surface property detection device for mounting in a vehicle, comprising
   a sensor device having a radiation emitter directed towards the road surface and at least one detector for detecting the radiation reflected from the road surface and providing an output accordingly, and a data processing arrangement for processing the output from the at least one detector to determine surface properties of the road and providing an output accordingly,
   a transmission arrangement for receiving said output from the sensor device and conducting a wireless transmission of road surface property data based thereon to a receiver exterior to the vehicle,
wherein the device further comprises a wireless receiver arrangement adapted to receive radio transmissions of data from transmission arrangements of devices similar to the device itself, and
   a data output arrangement for receiving an input from the receiver arrangement and presenting an output perceivable by the driver of the vehicle based thereon.

2. The device according to claim 1, comprising
   a position arrangement for generating position data for estimation of the current position of the device,
wherein the transmission arrangement is arranged to transmit said position data.

3. The device according to claim 1, wherein the data output arrangement further is arranged for receiving an input from the detector and presenting an output perceivable by the driver of the vehicle based thereon.

4. The device according to claim 1, wherein the sensor device comprises
   a light source for emitting light towards the surface,
   a first detector arranged for receiving a portion of said emitted light when reflected from said surface and producing a first output according to the intensity thereof,
   a second detector arranged for receiving a portion of said emitted light when reflected from said surface and producing a second output according to the intensity thereof, and
   a control arrangement for receiving and evaluating the received output from the detectors based on the amount of diffuse reflected and mirror reflected light,
   a first linear polarization filter arranged in the path of the light from the light source and to the surface for the polarization of the emitted light, and
   a second linear polarization filter arranged in the path of the light between said surface and one of the first detector and the second detector.

5. The device according to claim 4, wherein the light source is arranged to emit light in a direction within 15-20° from the surface normal.

6. The device according to claim 4, wherein the direction of polarization of the second filter is parallel to the direction of polarization of the first filter.

7. The device according to claim 6, comprising a third polarization filter arranged in the path of the light between said surface and the other one of the first detector and the second detector, wherein the direction of polarization of the third filter is perpendicular to the direction of polarization of the first and the second filter.

8. The device according to claim 6, wherein the first and second filter are constituted by one linear polarization filter and a beam splitter is arranged between the first polarization filter and the light source for the diversion of a portion of the light reflected from the surface into said detector.

9. The device according to claim 4, further comprising a first beam splitter arranged in the path of the light from the first linear polarization filter and to the surface for the diversion of a portion of the light reflected from the surface into a second path, and a second beam splitter arranged in the second path for the diversion of a portion of the light in the second path into the first detector and the transmission of a portion of the light in the second path into the second detector.

10. The device according to claim 4, comprising a reference light source arranged to emit light substantially in the direction and path of the first light source, wherein the reference light source emits light of a wavelength on which said polarization filters of the device have substantially no effect, so that the detection of the light from the reference light source by the first and second detector may be used for verification of the function of the system.

11. The device according to claim 4, further comprising a light source for emitting light within the wavelength range of 930 nm to 970 nm towards the surface and an absorption detector for receiving the reflection of said emitted light and producing an output to the control arrangement accordingly.

12. The device according to claim 4, further comprising a light source for emitting light towards the surface, the path of the light having an angle in the range of 15° to 70° to the surface normal and a retro-reflection detector arranged for receiving the retro-reflection of said emitted light in said path and producing an output to the control arrangement accordingly.

13. The device according to claim 4, further comprising a light source for emitting polychromatic light towards the surface and at least two range detectors arranged to detect each a wavelength range of the reflection of said emitted light and producing an output to the control arrangement accordingly.

14. The device according to claim 13, comprising least three of said range detectors arranged to detect each a wavelength range of the reflection of said emitted light and producing an output to the control arrangement accordingly.

15. The device according to claim 13, wherein the said wavelength ranges each comprises a range within the visible wavelength range.

16. The device according to claim 4 for mounting in a vehicle, further comprising a noise sensor for receiving the noise from the vehicle travelling along a road and producing an output to the control arrangement accordingly.

17. The road surface property detection device, according to claim 1, to be mounted on a vehicle for contact-less detection of the surface properties of the road surface and providing an output accordingly, comprising a radiation emitter directed towards the road surface and at least one detector for detecting the radiation reflected from the road surface and providing an output accordingly,
wherein the device comprises a washing arrangement for the emitter and the at least one detector for recurrently flushing thereof.

18. The device according to claim 17, wherein said washing arrangement is connected to and operates concurrently with a windshield washer system of the vehicle.

19. The road surface property detection device according to claim 1, to be mounted on a vehicle for contact-less detection of the surface properties of the road surface and providing an output accordingly, comprising a radiation emitter directed towards the road surface and at least one detector for detecting the radiation reflected from the road surface and providing an output accordingly,
wherein at least one detector of the device comprises a shutter device for allowing a temporal access of radiation to the detector for a period of $1/10$ to $1/50,000$ seconds.

20. A system comprising
a plurality of devices according to claim 1, each mounted in a separate vehicle, and
a plurality of stationary detector arrangements for contact-less detection of the surface properties of the road surface and providing an output accordingly to transmission arrangements for receiving said output and conducting a wireless transmission of road surface property data based thereon to the receivers of said devices.

21. The system according to claim 20, comprising a plurality of stationary information arrangements having a receiver arrangement adapted to receive radio transmission data from the devices mounted in the vehicles as well as the stationary detector arrangements, and comprising visual communication devices arranged along roads for distributing information to the drives of vehicles on said roads based on said received road surface property data.

* * * * *